US011832950B2

(12) United States Patent
Dodemont

(10) Patent No.: US 11,832,950 B2
(45) Date of Patent: Dec. 5, 2023

(54) MUSCLE ACTIVITY MONITORING

(71) Applicant: Repono Pty Ltd, Bardon (AU)

(72) Inventor: Nicholas Dodemont, Bardon (AU)

(73) Assignee: REPONO PTY LTD

( * ) Notice: Subject to any disclaimer, the term of this patent is extended or adjusted under 35 U.S.C. 154(b) by 214 days.

(21) Appl. No.: 17/174,302

(22) Filed: Feb. 11, 2021

(65) Prior Publication Data

US 2021/0177336 A1 Jun. 17, 2021

Related U.S. Application Data

(63) Continuation of application No. 15/560,476, filed as application No. PCT/AU2016/050203 on Mar. 22, 2016, now Pat. No. 10,945,629.

(30) Foreign Application Priority Data

Mar. 23, 2015 (AU) ................................. 2015901026

(51) Int. Cl.
*A61B 5/00* (2006.01)
*A61B 5/296* (2021.01)
(Continued)

(52) U.S. Cl.
CPC ............ *A61B 5/296* (2021.01); *A61B 5/0816* (2013.01); *A61B 5/30* (2021.01); *A61B 5/316* (2021.01);
(Continued)

(58) Field of Classification Search
CPC ......... A61B 5/296; A61B 5/0816; A61B 5/30; A61B 5/316; A61B 5/318; A61B 5/389;
(Continued)

(56) References Cited

U.S. PATENT DOCUMENTS 6,516,289 B2 * 2/2003 David .................. A61B 5/4041
600/490
7,559,902 B2 * 7/2009 Ting ...................... A61B 5/296
600/300

(Continued)

FOREIGN PATENT DOCUMENTS

DE 202015001313 5/2015
EP 1547521 6/2005

(Continued)

OTHER PUBLICATIONS

Merritt, et al., Fabric-Based Active Electrode Design and Fabrication for Health Monitoring Clothing, IEEE Transactions on Information Technology in Biomedicine, vol. 13, No. 2, Mar. 2009, pp. 274-280.

(Continued)

*Primary Examiner* — May A Abouelela
(74) *Attorney, Agent, or Firm* — Booth Udall Fuller, PLC; Kenneth C. Booth

(57) ABSTRACT

A system for monitoring muscle activity of a biological subject, the system including at least one garment including a number of arrays of electrodes positioned on the garment so that when the garment is worn by a subject in use, the electrodes contact skin of the subject and generate electrical signals indicative of electrical potentials within respective muscles of the subject and at least one electronic processing device that processes signals from the electrodes in each electrode array to determine a muscle activation for parts of the respective muscles and uses the muscle activation to determine at least one muscle indicator indicative of muscle activity of the subject.

19 Claims, 11 Drawing Sheets

(51) Int. Cl.
  *A61B 5/08* (2006.01)
  *A61B 5/30* (2021.01)
  *A61B 5/316* (2021.01)
  *A61B 5/318* (2021.01)
  *A61B 5/389* (2021.01)
  *A61B 5/22* (2006.01)

(52) U.S. Cl.
  CPC .............. *A61B 5/318* (2021.01); *A61B 5/389* (2021.01); *A61B 5/6804* (2013.01); *A61B 5/6805* (2013.01); *A61B 5/6823* (2013.01); *A61B 5/6828* (2013.01); *A61B 5/7246* (2013.01); *A61B 5/742* (2013.01); *A61B 5/224* (2013.01); *A61B 2562/0215* (2017.08); *A61B 2562/046* (2013.01)

(58) Field of Classification Search
  CPC ... A61B 5/6804; A61B 5/6805; A61B 5/6823; A61B 5/6828; A61B 5/7246; A61B 5/742; A61B 5/224; A61B 2562/0215; A61B 2562/046
  See application file for complete search history.

(56) References Cited

U.S. PATENT DOCUMENTS

| | | | |
|---|---|---|---|
| 7,797,039 B2* | 9/2010 | Koivumaa | A61B 5/25 600/382 |
| 7,869,646 B2 | 1/2011 | Park et al. | |
| 7,912,526 B2 | 3/2011 | Finneran et al. | |
| 8,301,237 B2* | 10/2012 | Lanfermann | A61B 5/389 600/546 |
| 8,747,336 B2* | 6/2014 | Tran | A61B 8/565 600/595 |
| 9,285,788 B2 | 3/2016 | Nicoletti | |
| 9,589,374 B1 | 3/2017 | Gao et al. | |
| 10,082,830 B2* | 9/2018 | Lettow | B62D 1/06 |
| 2008/0004904 A1* | 1/2008 | Tran | A61B 5/411 340/286.07 |
| 2008/0192116 A1 | 8/2008 | Tamir et al. | |
| 2009/0088652 A1 | 4/2009 | Tremblay | |
| 2009/0318779 A1* | 12/2009 | Tran | A61B 5/411 600/595 |
| 2010/0069736 A1 | 3/2010 | Finneran et al. | |
| 2010/0106044 A1* | 4/2010 | Linderman | A61B 5/7264 600/546 |
| 2010/0113910 A1* | 5/2010 | Brauers | A61B 5/6887 600/382 |
| 2011/0166491 A1* | 7/2011 | Sankai | A41D 13/1281 601/84 |
| 2012/0172682 A1* | 7/2012 | Linderman | G06F 3/015 600/300 |
| 2013/0317648 A1* | 11/2013 | Assad | A61B 5/389 700/258 |
| 2014/0039571 A1 | 2/2014 | Wolpaw | |
| 2014/0135593 A1 | 5/2014 | Jayalth et al. | |
| 2014/0135960 A1 | 5/2014 | Choi | |
| 2014/0318699 A1* | 10/2014 | Longinotti-Buitoni | H05K 1/038 156/247 |
| 2015/0057984 A1 | 2/2015 | Nicoletti et al. | |
| 2015/0105641 A1* | 4/2015 | Austin | A61H 9/0078 600/300 |
| 2015/0272501 A1 | 10/2015 | MacEachern et al. | |
| 2015/0366504 A1* | 12/2015 | Connor | |
| 2016/0051182 A1* | 2/2016 | Zabaleta Rekondo | A61B 5/389 600/388 |
| 2017/0147905 A1 | 5/2017 | Huang et al. | |

FOREIGN PATENT DOCUMENTS

| | | |
|---|---|---|
| EP | 2289402 | 3/2011 |
| WO | 2009/014309 | 1/2009 |
| WO | 2012/140522 | 10/2012 |
| WO | 2013/006644 | 1/2013 |
| WO | 2015/195209 | 12/2013 |
| WO | 2014/016547 | 1/2014 |
| WO | 2014/080403 | 5/2014 |
| WO | 2017120669 | 7/2017 |
| WO | 2017133009 | 8/2017 |

OTHER PUBLICATIONS

"Wearable silver nanowire dry electrodes for electrophysiological sensing" by Amanda C. Myers, He Huang and Yong Zhu in RSC Adv., 2015, 5, 11627-11632.

"The Effects of Electrode Size and Orientation on the Sensitivity of Myoelectric Pattern Recognition Systems to Electrode Shift" by Aaron J. Young published in IEEE Transactions on Biomedical Engineering, vol. 58, No. 9, Sep. 2011.

"Techniques of EMG signal analysis: detection, processing, classification and applications" by M.B.I. Raez, M.S. Hussain and F. Mohd-Yasin in Biol Proced Online. 2006; 8: 11-35.

"Advances in Surface EMG: Recent Progress in Detection and Processing Techniques" by Roberto Merletti, Matteo Aventaggiato, Alberto Botter, Ales Holobar, Hamid Marateb and & Taian M.M. Vieira; Critical Reviews in Biomedical Engineering, 38(4): 305-345 (2010).

"Accurate identification of motor unit discharge patterns from high-density surface EMG and validation with a novel signal-based performance metric" by A Holobar, M A Minetto and D Farina; J. Neural Eng. 11 (2014) 016008 (11pp).

"A real-time, practical sensor fault-tolerant module for robust EMG pattern recognition" by Xiaorong Zhang and He Huang; Journal of NeuroEngineering and Rehabilitation (2015) 12:18.

De Luca CJ, et al, Inter-electrode spacing of surface EMG sensors: Reduction of cross talk contamination during voluntary contractions, Journal of Biomechanics 45 (2012), 555-561.

R. Merletti, A. Botter, U. Barone; Detection and Conditioning of Surface EMG Signals; Laboratory for Engineering of the Neuromuscular System, Politecnico di Torino, Torino, Italy.

R. Merletti (Laboratory for Engineering of the Neuromuscular System, Politecnico di Torino, Torino, Italy), T.M. Vieira (Escolade Educação Físicae Desportos, Universidade Federaldo Rio de Janeiro, Rio deJ aneiro, Brasil), D. Farina (Department of Neurorehabilitation Engineering, Bernstein Focus Neurotechnology Göttingen, University Medical Center Göttingen, Georg-August University, Göttingen, Germany; Techniques for Information Extraction From the Surface EMG Signal: High-Density Surface EMG.

E.A.Clancy (Electrical & Computer Engineering Department; Biomedical Engineering Department, Worcester Polytechnic Institute, Worcester, Massachusetts), F. Negro and D.Farina (Department of Neurorehabilitation Engineering, Bernstein Center for Computational Neuroscience, University Medical Center Goettingen, Goettingen, Germany); Single-Channel Techniques for Information Extraction From the Surface EMG Signal.

* cited by examiner

MUSCLE ACTIVITY MONITORING

CROSS REFERENCE TO RELATED APPLICATIONS

This application is a continuation of U.S. application Ser. No. 15/560,476, filed Sep. 21, 2017, now pending, which application is a U.S. National Stage of International Application No. PCT/AU2016/050203, filed Mar. 22, 2016, which claims the benefit of and priority to Australian Patent Application No. 2015901026, filed Mar. 23, 2015, the contents of each of which are hereby incorporated by reference in their entireties.

BACKGROUND OF THE INVENTION

The present invention relates to a system and method for monitoring the muscle activity of a subject, and in particular to a system for monitoring muscle activity of a subject using at least one garment worn by the subject in use.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Whilst it is known to provide devices for monitoring activity, these are generally limited to detecting movement through the use of movement sensors, which does not accurately track muscle activity. Measuring muscle activity by recording electrical signals from muscles, in a process commonly referred to as EMG (Electromyography) is known, this generally uses needle electrodes inserted into the muscles of the subject, which is therefore restrictive and therefore only used in limited situations.

SUMMARY OF THE PRESENT INVENTION

In one broad form the invention seeks to provide a system for monitoring muscle activity of a biological subject, the system including:
 a) at least one garment including a number of arrays of electrodes positioned on the garment so that when the garment is worn by a subject in use, the electrodes contact skin of the subject and generate electrical signals indicative of electrical potentials within respective muscles of the subject; and,
 b) at least one electronic processing device that:
  i) processes signals from the electrodes in each electrode array to determine a muscle activation for parts of the respective muscles; and,
  ii) uses the muscle activation to determine at least one muscle indicator indicative of muscle activity of the subject.

In another broad form the invention seeks to provide a method for monitoring muscle activity of a biological subject, the method including:
 a) providing the subject with at least one garment including a number of arrays of electrodes positioned on the garment so that when the garment is worn by the subject, the electrodes contact skin of the subject and generate electrical signals indicative of electrical potentials within respective muscles of the subject; and,
 b) in at least one electronic processing device:
  i) processing signals from the electrodes in each electrode array to determine a muscle activation for parts of the respective muscles; and,
  ii) using the muscle activation to determine at least one muscle indicator indicative of muscle activity of the subject.

In another broad form the invention seeks to provide a garment for use in monitoring muscle activity of a biological subject, the garment including a number of arrays of electrodes positioned on the garment so that when the garment is worn by a subject in use, the electrodes contact skin of the subject and generate electrical signals indicative of electrical potentials within respective muscles of the subject.

Typically the muscle activation is indicative of at least one of a magnitude and frequency of muscle activation.

Typically the muscle indicator includes at least one of:
 a) an intramuscular indicator indicative of muscle activation within a muscle;
 b) an intermuscular indicator indicative of a relative muscle activation of contralateral muscles on contralateral limbs;
 c) an efficiency indicator indicative of the relative efficiency of muscle activation of muscles; and,
 d) a muscle fatigue indicator indicative of a muscle fatigue.

Typically the at least one processing device, for each muscle:
 a) determines an average muscle activation;
 b) compares the muscle activation of parts of the muscle to the average muscle activation; and,
 c) determines an intramuscular indicator at least in part using results of the comparison.

Typically the at least one processing device, for each pair of contralateral muscles:
 a) compares the muscle activation of each muscle in the pair; and,
 b) determines an intermuscular indicator at least in part using results of the comparison.

Typically the at least one processing device:
 a) determines a muscle activation pattern indicative of the muscle activation of each of a number of muscles;
 b) compares the muscle activation pattern to a reference muscle activation pattern; and,
 c) determines an efficiency indicator at least in part using the results of the comparison.

Typically the at least one processing device:
 a) determines an activity being performed by the subject; and,
 b) selects one of a number of predefined reference activation patterns at least partially in accordance with the determined activity.

Typically the at least one processing device determines the activity being performed at least one of:
 a) by analysing muscle activation patterns; and,
 b) in accordance with user input commands.

Typically the at least one processing device selects one of a number of predefined reference activation patterns in accordance with subject parameters including at least one of:
 a) a subject age;
 b) a subject sex;
 c) a subject weight;
 d) a subject height; and,
 e) a subject fitness level.

Typically the predefined reference activation patterns include a previous recorded activation pattern for the subject.

Typically the at least one processing device:
a) determines a current muscle activation pattern indicative of the muscle activation of each of a number of muscles;
b) determines previous muscle activation patterns;
c) identifies a historical activation based on at least one of a mean and maximum of the previous muscle activation patterns;
d) compares the current muscle activation pattern to the historical activation pattern; and,
e) determines a fatigue indicator at least in part using the results of the comparison.

Typically the at least one processing device:
a) generates a representation at least partially based on the at least one muscle indicator; and,
b) causes the representation to be displayed to a user.

Typically the representation includes at least one of:
a) an alphanumeric indication of the at least one muscle indicator;
b) a graphical representation of a muscle activation pattern for at least one muscle; and,
c) a graphical representation of results of a comparison of a muscle activation pattern to a reference muscle activation pattern.

Typically the electrodes are at least one of:
a) conductive fabric electrodes woven into the garment; and,
b) dry electrodes provided in the garment.

Typically the electrodes are at least one of:
a) silver plated nylon electrodes; and,
b) silver plated nanowire electrodes.

Typically each array of electrodes includes a plurality of electrodes arranged in a grid.

Typically each electrode has a surface area that is at least one of:
a) between 0.5 cm$^2$ and 3.0 cm$^2$;
b) between 0.75 cm$^2$ and 1.5 cm$^2$;
c) about 0.75±0.25 cm$^2$;
d) about 1.0±0.25 cm$^2$;
e) about 1.25±0.25 cm$^2$;
j) about 1.5±0.25 cm$^2$;
g) about 1.75±0.25 cm$^2$;
h) about 2.0±0.25 cm$^2$;
i) about 2.5±0.5 cm$^2$; and,
j) about 1 cm$^2$.

Typically electrodes in the array are spaced by at least one of:
a) between 0.5 cm and 2.0 cm;
b) between 0.75 cm and 1.75 cm;
c) between 1.0 cm and 1.5 cm;
d) about 0.75±0.25 cm;
e) about 1.0±0.25 cm;
f) about 1.25±0.25 cm; and,
g) about 1.5±0.25 cm.

Typically each electrode in the electrode array is electrically connected to a connector, the connector being for coupling the electrodes to the at least one processing device.

Typically at least one processing device is mounted in a pocket provided on the garment, the connector being provided at least partially within the pocket.

Typically each electrode in the electrode array is electrically connected to the connector via nanowires woven into the garment.

Typically the garment includes at least one of:
a) pants for covering at least the groin and upper legs of the user; and,
b) a shirt for covering at least the torso of the user.

Typically the garment includes elasticated material to thereby urge the electrodes against the subject's skin.

Typically the garment is made of at least one of:
a) polyamides;
b) polyester; and,
c) elastane.

Typically each array of electrodes is aligned with a respective muscle or muscle group.

Typically the muscle or muscle groups include at least one of:
a) trapezius;
b) rhomboids;
c) latissimus dorsi;
d) erector spinae;
e) rotator cuff muscles (including supraspinatus, infraspinatus, subscapularis, teres minor/major); f) forearm extensors/flexors;
g) tibialis anterior/posterior;
h) thoracic paraspinals;
i) lumbar paraspinals;
j) biceps;
k) triceps;
l) quadriceps;
m) hamstrings;
n) adductors;
o) gluteals;
p) calves;
q) abdominals;
r) deltoids; and,
s) pectorals.

Typically system includes a measuring device, the measuring device including:
a) a voltage sensor coupled to the electrodes for sensing electrical potentials between pairs of electrodes; and,
b) at least one processing device coupled to the voltage sensor for receiving signals indicative of the sensed voltages.

Typically the voltage sensor includes:
a) a differential amplifier for amplifying analogue electrical signals obtained from a pair of electrodes; and,
b) an A/D convertor for converting an amplified differential voltage into a digital voltage signal, the digital voltage signal being provided to the at least one processing device for processing.

Typically the measuring device includes a filter for filtering electrical signals.

Typically the measuring device includes a switching device for selectively coupling the voltage sensor to respective pairs of electrodes in each array.

Typically the switching device is controlled at least in part by the at least one processing device.

Typically the system includes:
a) a first electronic processing device attached to or worn by the subject that:
  i) acquires signals from the sensors;
  ii) at least partially processes the signals; and,
b) a second processing device that wirelessly communicates with the first processing device and displays a representation at least partially based on the at least one muscle indicator.

Typically the system includes an ECG sensor for sensing cardiac activity of the subject and wherein the at least one electronic processing device:
a) acquires signals from the ECG sensor; and,
b) determines a cardiac indicator indicative of cardiac activity of the subject.

Typically the system includes a respiratory sensor for sensing respiratory activity of the subject and wherein the at least one electronic processing device:
a) acquires signals from the respiratory sensor; and,
b) determines a respiratory indicator indicative of respiratory activity of the subject.

Typically the at least one electronic processing device determines an activity indicator indicative of an overall activity of the subject using:
a) the at least one muscle indicator; and,
b) at least one of:
  i) a cardiac indicator indicative of cardiac activity of the subject; and,
  ii) a respiratory indicator indicative of respiratory activity of the subject.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1A:
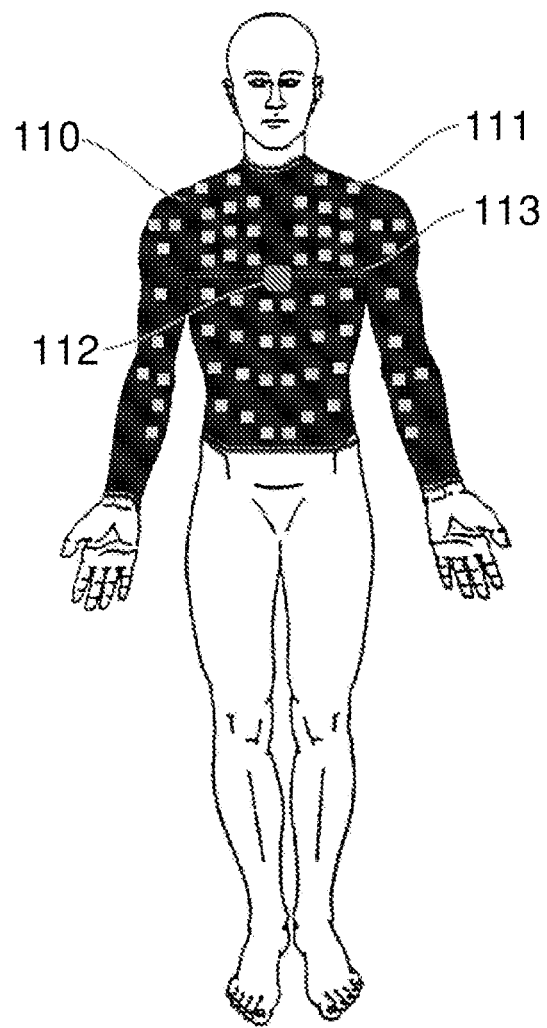
FIG. 1A is schematic diagram of a first garment for use in monitoring muscle activity of a biological subject.
Figure 1B:
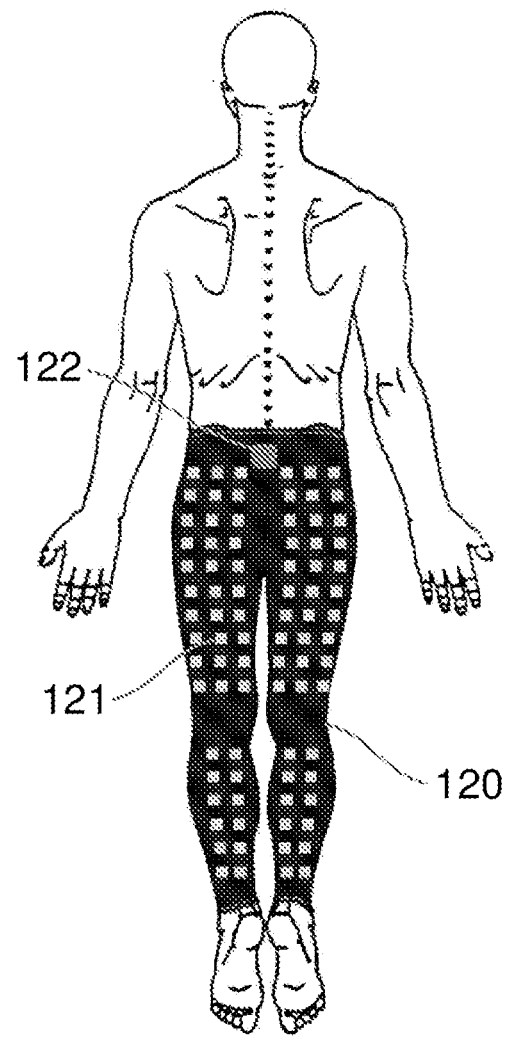
FIG. 1B is schematic diagram of a second garment for use in monitoring muscle activity of a biological subject.

Examples of garments for use in monitoring muscle activity of a subject are shown in FIGS. 1A and 1B.

The garments 110, 120 each include a number of arrays of electrodes 111, 121 positioned on the garment 110, 120 so that when the garment is worn by a subject in use, the electrodes contact skin of the subject and generate electrical signals indicative of electrical potentials within respective muscles of the subject. In this example, the garments are in the form of a shirt 110 for covering at least the torso and parts of the arms of the user and pants 120 for covering at least the groin and upper legs of the user, although other suitable arrangements can be used as will be described in more detail below.

In use, the electrodes 111, 121 are electrically connected to at least one processing device that operates to process signals and determine at least one muscle activity indicator. The at least one processing device could be of any suitable form, and could include a wearable custom or off the shelf processing device and/or a suitably programmed general purpose processing system, such as a computer system, smart phone, smartwatch, tablet or the like.

Figure 2:
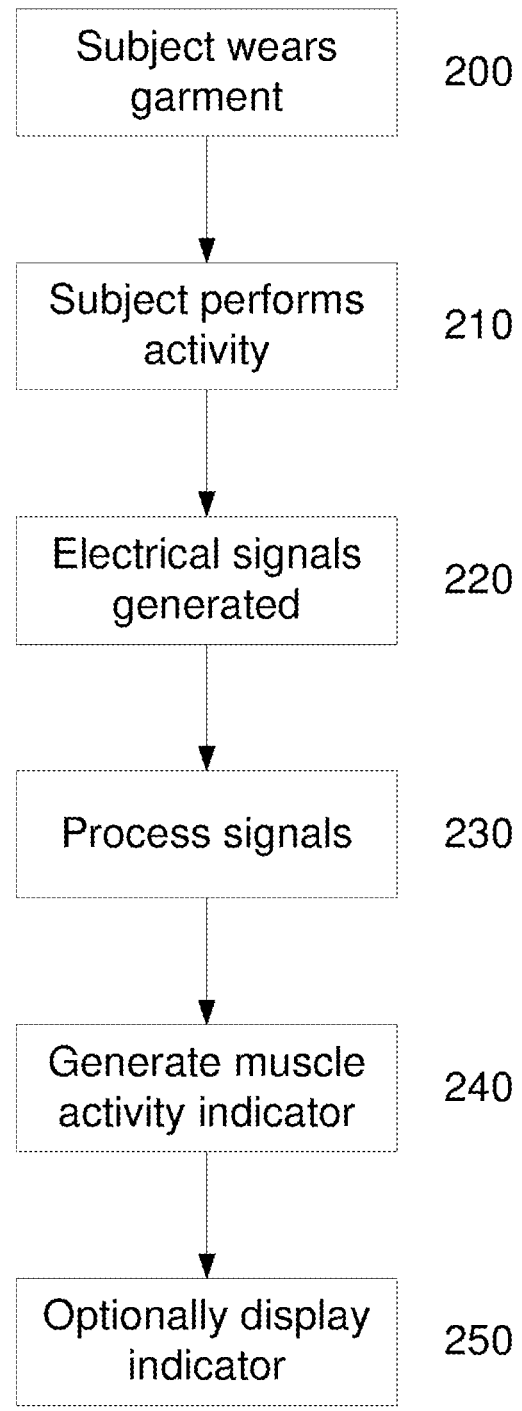
FIG. 2 is a flow chart of an example of a method for monitoring muscle activity of a biological subject.

An example of a method of use of the system will now be described with reference to FIG. 2.

In this example, at step 200, the subject wears the garment(s) and performs activities at step 210. The activities could be of any suitable form depending on the preferred implementation or use. For example, if the subject is an athlete or sports person, the activities could include exercises, participating in a sporting event, training or the like. Alternatively, the subject may be undergoing monitoring as part of a medical assessment, for example to assess muscle strength and movement patterns in individuals having muscular or neurological conditions such as myolysis, myasthenia gravis, muscular dystrophy, or the like, in which case the activities could include day-to-day activities, defined sequences of movements, exercises or the like.

At step 220, the electrodes 111, 121 generate electrical signals based on electrical activity within the subject's muscles, with the processing device processing these signals at step 230 to determine a muscle activation for parts of the respective muscles. The muscle activation is indicative of the degree of electrical activity within the respective parts of the muscle and in particular at least one of the frequency and/or magnitude of activation, and therefore corresponds broadly to the amount of work being performed by the respective part of the muscle. Thus, signals from different pairs of electrodes within each array are used to determine a degree of muscle activation for different parts of muscles within each muscle or muscle group.

At step 240, the processing device uses the muscle activation to determine at least one muscle indicator indicative of muscle activity of the subject, with the indicator being optionally displayed at step 250.

The indicator can be of any suitable form, and can include a number of different indicators examining different aspects of muscle activity. For example, the system can be used to determine any one or more of an intramuscular indicator indicative of muscle activation within a muscle, an intermuscular indicator indicative of a relative muscle activation of contralateral muscles on contralateral limbs, an efficiency indicator indicative of the relative efficiency of muscle activation of muscles when performing a task, and a muscle fatigue indicator indicative of a muscle fatigue. However, these examples are not intended to be limiting and additional and/or alternative indicators could be used depending on the preferred implementation. Specific example indicators and techniques for their derivation will be described in more detail below.

The above described steps can be performed periodically or continuously as a subject performs exercise. For example, the system could continuously monitor muscle activity, and display indicators in real time, allowing an individual to use these as feedback while performing activity. Additionally and/or alternatively, indicators and raw data could be stored, allowing these to be subsequently reviewed after the activity has been performed.

In any event, it will be appreciated that the indicators can be used to assess a wide range of different aspects of muscle activity, including for example whether the subject is using their muscles effectively, whether the muscles are functioning as expected/required, whether the subject is fatigued, whether the muscles are injured and/or at risk of injury, or the like.

Accordingly, the above described system and process allows a subject's muscle activation to be monitored, whilst the subject performs different activities, in turn allowing a muscle activity indicator to be determined. By allowing this to be performed using garments incorporating arrays of electrodes, this allows monitoring to be performed during a range of different activities, including sport, exercise and/or day-to-day activities, without impeding the subject. Additionally, through suitable arrangement of the electrodes, this allows information regarding the activation of different parts of different muscles to be monitored, allowing a range of different indicators to be derived, which can in turn be used to assess muscle function. This can be used for medical purposes, for example as part of the diagnosis and/or treatment of medical conditions, as well as for activity monitoring, for example to examine muscle activity of a participant in a sporting event to ensure the participant is functioning optimally.

As part of this, it will be appreciated that the indicator could be further used as part of general fitness tracking, for example by monitoring total muscle activity during a workout, which in turn can allow a more accurate assessment of calories burned to be made.

A number of further features will now be described.

The electrodes are typically integrally formed within the garment, and could include any suitable conductive dry electrodes, which may for example be woven into the garment as conductive fabric electrodes. In one particular example the electrodes are silver plated nylon electrodes, or the like, examples of which are described in WO2014/080403. However, it will be appreciated that any conductive or metal coated fabric or nanowire could be used. For example, the electrodes could be silver plated nanowire electrodes provided on an elastomeric substrate, such as polydimethylsiloxane (PDMS), similar to those described in "Wearable silver nanowire dry electrodes for electrophysiological sensing" by Amanda C. Myers, He Huang and Yong Zhu in RSC Adv., 2015, 5, 11627-11632|11627. This allows the electrodes to remain as part of the garment whilst the garment is washed, making the system readily useable in a variety of situations. Alternatively, electrodes could be screen printed or applied using any other suitable technique and could include using a stretchable resin base material with a conductive paste to provide a flexible electrode.

The garment is typically made of an elasticated material, which helps urge the electrodes against the subject's skin, avoiding the need for any adhesive, conductive gel, or the like, whilst ensuring good electrical contact between the electrodes and the subject's tissue, which is in turn important in ensuring accurate measurements are collected. The garment can be made of any suitable material, but is typically made of a mixture of polyamides and elastane, in the form of an elasticated compressive garment, similar to those marketed under the trade name Skins™. This is particularly beneficial as this allows the subject to simply wear the garment as though it were part of their normal sporting attire, whilst also providing the benefit of such garments. However, it will be appreciated that other materials could be used such as polyester, or the like.

Each array of electrodes typically includes at least two electrodes, and more typically a plurality of electrodes arranged in a grid. The electrodes typically have a surface area that is between 0.5 $cm^2$ and 3.0 $cm^2$, between 0.75 $cm^2$ and 1.5 $cm^2$, about 0.75±0.25 $cm^2$, about 1.0±0.25 $cm^2$, about 1.25±0.25 $cm^2$, about 1.5±0.25 $cm^2$, about 1.75±0.25 $cm^2$, about 2.0±0.25 $cm^2$, about 2.5±0.5 $cm^2$, and more typically about 1 $cm^2$. The electrodes can be of any shape and could include circular electrodes having a diameter of between 0.5 cm and 1.5 cm, and more typically about 1 cm. The electrodes are typically separated by between 0.5 cm and 2.0 cm, between 0.75 cm and 1.75 cm and between 1.0 cm and 1.5 cm, about 0.75±0.25 cm, about 1.0±0.25 cm, about 1.25±0.25 cm, about 1.5±0.25 cm, or approximately 2 cm between centres of adjacent electrodes, although alternative spacings could be used depending on the required resolution of the measurements. In this regard, it will be appreciated that different electrode sizes and/or spacings could be used to vary the resolution of the measurements, allowing measurements to be performed up to and include of muscle fibres connected to a single neural pathway ending. This allows the firing of individual neural muscle connections to be monitored. Further issues regarding electrode sizing and spacing can be found in "The Effects of Electrode Size and Orientation on the Sensitivity of Myoelectric Pattern Recognition Systems to Electrode Shift" by Aaron J. Young published in IEEE TRANSACTIONS ON BIO-MEDICAL ENGINEERING, VOL. 58, NO. 9, September 2011.

Each electrode in the electrode array is electrically connected to a connector, for example via a respective conductive path running from the electrode to the connector. The conductive path can be formed of any appropriate conductive material, but in one example is made of conductive nanowires woven into the fabric. Such nanowires, typically made of coated nano tubes, are particularly advantageous as they are thin and flexible, allowing the garment to maintain its wearable characteristics, whilst being strong, resulting in a greater lifespan.

The connector is used for electrically connecting the electrodes to the at least one processing device. In this regard, the at least one processing device can be mounted in a pocket 112, 122 provided on the garment, with the connector being provided at least partially within the pocket. This allows the processing device to be easily connected/disconnected to the electrodes and hence removed from the garment as required, for example to allow the garment to be washed. This could be achieved using a "clip-in" arrangement, so that the processing device connects to the connector upon insertion into the pocket, although any suitable arrangement could be used.

As shown in FIGS. 1A and 1B, the garment can include pants 120 for covering at least the groin and upper legs of the user or a shirt 110 for covering at least the torso of the user. It will be appreciated that other suitable arrangements could be used, such as fully body torso or leggings.

Each array of electrodes is typically aligned with a respective muscle or muscle group, including but not limited to any one or more of trapezius, rhomboids, latissimus dorsi, erector spinae, rotator cuff, forearm extensors/flexors, tibialis anterior/posterior, thoracic paraspinals, lumbar paraspinals, biceps, triceps, quadriceps, hamstrings, adductors, gluteals, calves, abdominals, deltoids and pectorals. It will be appreciated that the particular configuration used may depend on the intended application, and in particular which muscles are of interest from the perspective of monitoring.

The muscle activation can be determined from the signals generated by the electrodes in any suitable manner. For example, the muscle activation can be indicative of at least one of a magnitude and frequency of the signals, and can be determined using appropriate signals processing techniques, such as Fourier analysis or the like. It will be appreciated from this that the signals are Electromyography (EMG) signals, and accordingly appropriate signal processing techniques used for EMG could be employed.

Having determined the muscle activation, additional processing is performed in order to determine the indicators. The nature of the processing will depend on the type of indicator being derived.

For example, to determine an intramuscular indicator the processing device typically determines an average muscle activation, compares the muscle activation of parts of the muscle to the average muscle activation and determines an intramuscular indicator at least in part using results of the comparison. Thus, this will identify if activation is relatively constant across the entire muscle, or whether some distinct parts of the muscle are undergoing greater or lesser activation, which can be useful in identifying potential injuries and/or muscle damage.

To determine an intermuscular indicator, the processing device compares the muscle activation of each muscle in a pair of contralateral muscles and then determines the intermuscular indicator at least in part using results of the comparison. Thus, this examines whether contralateral muscles, such as the hamstrings in each leg, are activating to a similar degree, or whether one muscle is being favoured over the other, which can in turn be indicative of injury, or an imbalance in muscle use.

To determine an efficiency indicator, the processing device can determine a muscle activation pattern indicative of the muscle activation of each of a number of muscles, compare the muscle activation pattern to a reference muscle activation pattern and, determine an efficiency indicator at least in part using the results of the comparison. Thus, this can use predefined muscle activation patterns to assess whether the subject's muscles are activating in an optimum pattern. The predefined muscle activations are typically defined based on a range of factors, such as the activities being performed, and characteristics of the subject.

Thus, the processing device typically determines an activity being performed by the subject and selects one of a number of predefined reference activation patterns at least partially in accordance with the determined activity. In this regard, it will be appreciated that a different activation pattern would be expected if the subject is performing squats, as opposed to running or jumping. Accordingly, by determining the activity being performed, this allows the processing device to select the most appropriate reference activation pattern. The processing device can determine the activity being performed using any suitable approach, such as analysing muscle activation patterns and/or in accordance with user input commands, or the like. Thus, the processing device can monitor the muscle activation patterns to automatically determine the particular activity being performed, without requiring input from the user. This would typically be performed by comparing measured muscle activity patterns to defined patterns representing different activities.

Additionally, the reference muscle activation pattern can be selected based on subject parameters, defining characteristics of the subject, such as a subject age, a subject sex, a subject weight, a subject height and a subject fitness level. Thus, different reference patterns could be established for different groups of individuals, allowing the muscle activation pattern of the subject to be compared to patterns of similar individuals performing similar activities. Thus, the activity pattern recorded for other individuals can be used to establish an idealised baseline as the reference activity pattern, with the subject's activity being compared to this to identify deviation from the baseline.

Additionally and/or alternatively the reference activation pattern can include a previous recorded activation pattern for the subject. This can be useful, for example, to monitor improvement and/or worsening of muscle activation during certain activities. This can be used to identify improvements as a result of training, medical intervention or rehabilitation, or problems arising, for example due to progression of muscle related disorders. Such prior activation patterns could be stored as part of a user profile, stored either locally on the processing device, or remotely, for example in a cloud or network based store.

The processing device can determine a fatigue indicator by determining a current muscle activation pattern indicative of the muscle activation of each of a number of muscles, determining previous muscle activation patterns, identifying a historical activation based on at least one of a mean and maximum of the previous muscle activation patterns, comparing the current muscle activation pattern to the historical activation pattern and determining a fatigue indicator at least in part using the results of the comparison. Thus, this allows changes in muscle activation over time to be used to determine a level of a fatigue. In one example, this process is performed at least partially based on the frequency of muscle activation, which is a known indicator of muscle fatigue, as will be described in more detail below.

It will be appreciated form the above that the system can use a wide range of different analysis techniques in order to analyse the muscle activation signals and determine one or more muscle indicators. This could include pattern recognition, in which muscle activation patterns are compared to reference or previously measured activation patterns. Alternatively, this could involve performing component analysis, such as principle component analysis (PCA) in order to identify components of the muscle activation signals, and hence derive the indicators therefrom. For example, this could involve analysing signal amplitude, frequency, gradients, or the like, and using these to determine the muscle indicators.

Typically the processing device generates a representation at least partially based on the indicator and causes the representation to be displayed to a user. This allows the one or more indicators to be displayed to a user, allowing the user to view the current muscle activation of the subject. In this regard, it will be appreciated that the subject could be the user, although this is not essential and alternatively the user could be a third party that is monitoring or observing the subject. For example, the user could be a medical practitioner reviewing monitoring the muscle health or activity levels of a patient. Alternatively, the user could be a coach or trainer monitoring the muscle activity of a trainee, such as an athlete or the like.

The representation could be of any suitable form but typically includes an alphanumeric indication of the indicator, a graphical representation of a muscle activation pattern for at least one muscle and/or a graphical representation of results of a comparison of a muscle activation pattern to a reference muscle activation pattern. Different representations could be used for different indicators, and typically the user would have the ability to select a desired representation type.

Whilst the system can use a single processing device, such as a single worn processing system, more typically functionality is distributed between multiple processing devices. In this case, the system typically includes a first electronic processing device attached to or worn by the subject that acquires signals from the sensors and at least partially processes the signals and a second processing device that wirelessly communicates with the first processing device and displays a representation at least partially based on the indicator. This allows monitoring of the subject to be performed remotely, without impeding the subject. This also allows more computationally expensive operations to be handled remotely to the subject, minimising the hardware requirements of the device worn by the user.

In one particular example, the first processing device is part of a measuring device including a voltage sensor coupled to the electrodes for sensing electrical potentials between pairs of electrodes and at least one processing device coupled to the voltage sensor for receiving signals indicative of the sensed voltages, and at least partially processing these, for example to determine signal parameters. The measuring device is typically mounted within the pocket, and is adapted to communicate with a separate remote second processing device, for example forming part of a host device, such as a smart phone, tablet or the like, allowing representations of the indicator to be viewed thereon.

From this it will be appreciated that the measuring device can be a lightweight portable battery operated unit that is worn by the subject during activity, with the host device being provided remotely allowing the muscle activity of the subject to be monitored.

The voltage sensor typically includes a differential amplifier for amplifying analogue electrical signals obtained from a pair of electrodes and an A/D convertor for converting an amplified differential voltage into a digital voltage signal, the digital voltage signal being provided to the at least one processing device for processing. The measuring device can also include a filter for filtering electrical signals, for example using an analogue anti-aliasing front end filter, or a bandpass filter in the digital domain to remove extraneous noise or other signal components. The measuring device can include a switching device for selectively coupling a single voltage sensor to respective pairs of electrodes in each array, or alternatively, multiple voltage sensors could be provided, with each being adapted to measure signals from a respective pair of electrodes. This allows readings to be obtained from different pairs of electrodes within each array, with this being controlled by the processing device within the measuring device.

The system can also include additional sensors to determine other physiological parameters. For example, the system can include an ECG sensor for sensing cardiac activity of the subject, with the processing device acquiring signals from the ECG sensor and determining a cardiac indicator indicative of cardiac activity of the subject. Similarly, the system can include a respiratory sensor for sensing respiratory activity of the subject, in which case the processing device typically acquires signals from the respiratory sensor and determines a respiratory indicator indicative of respiratory activity of the subject.

When cardiac and/or respiratory indicators are determined, the processing device can determine an activity indicator indicative of an overall activity of the subject using the at least one muscle indicator one or more of the cardiac indicator and respiratory indicator.

Figure 3A:
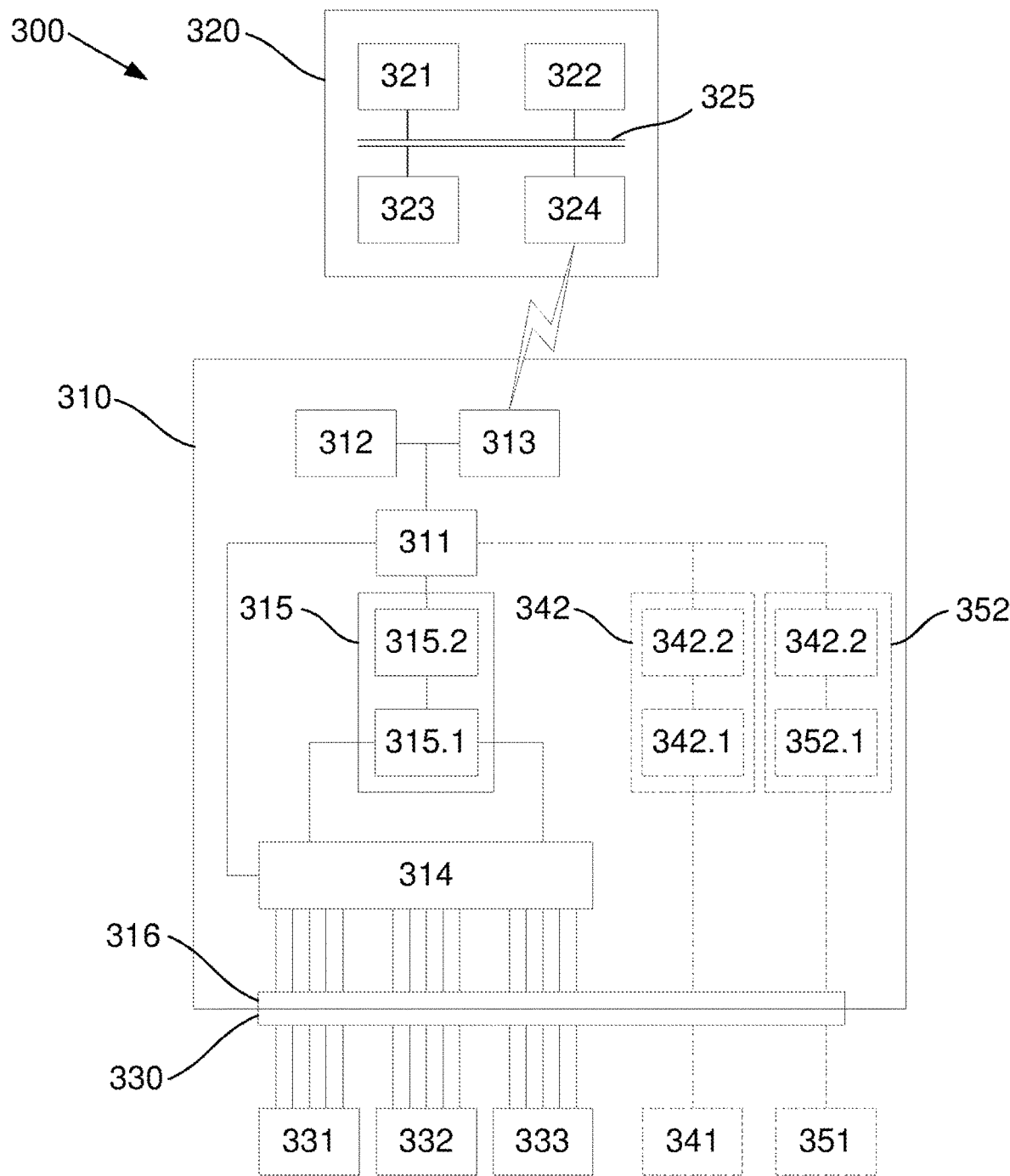
FIG. 3A is a schematic diagram of a first example of a system for use in monitoring muscle activity of a biological subject.

A specific example of the electronic components of the system will now be described in more detail with reference to FIG. 3A.

In this example, as previously described the system 300 includes a measuring device 310, which is adapted to be coupled to the garment and worn by the user, and a host device 320, which is in communication with the measuring device, to allow indicators to be displayed thereon.

In this example, the measuring device 310 includes a microprocessor 311, coupled to a memory 312 and an external interface 313, such as a wireless communications interface for communicating with the host device 320.

The measuring device 310 includes a switching device 314, such as a dual band multiplexer, which is coupled to respective electrode arrays 331, 332, 333, via a port 316 and corresponding connector 330 provided on the garment. Although three electrode arrays are shown, this is for the purpose of illustration only, and in practice any number of electrode arrays may be provided, depending on the preferred implementation.

The switching device 314 is also coupled to a voltage sensor 315, allowing signals from respective pairs of electrodes within the arrays to be provided thereto. The voltage sensor typically includes a differential amplifier 315.1, for amplifying a potential difference across the pair of electrodes and an analogue-to-digital convertor (ADC) 315.2 for digitising the resulting potential difference signal. An optional filter (not shown) is also provided for filtering the signals for example using a bandpass filter, to remove any signal components from other sources, such as noise in the leads, or other biological signals, such as ECG signals or the like. Accordingly, in use, the voltage sensor 315 amplifies the potential difference between the electrodes in the respective pair, and generates an analogue voltage signal, which is then filtered and digitised before being provided to the processor 311 for analysis.

In use, the processor 311 controls the switching device 314 to connect the differential amplifier to respective pairs of electrodes within a given electrode array 331, 332, 333, based on a defined measurement protocol. The measurement protocol typically defines a sequence of pairs of electrodes from which measurements should be taken, and may be stored in the memory 312 and selected depending on the desired outcome, as will be described in more detail below.

Figure 3B:
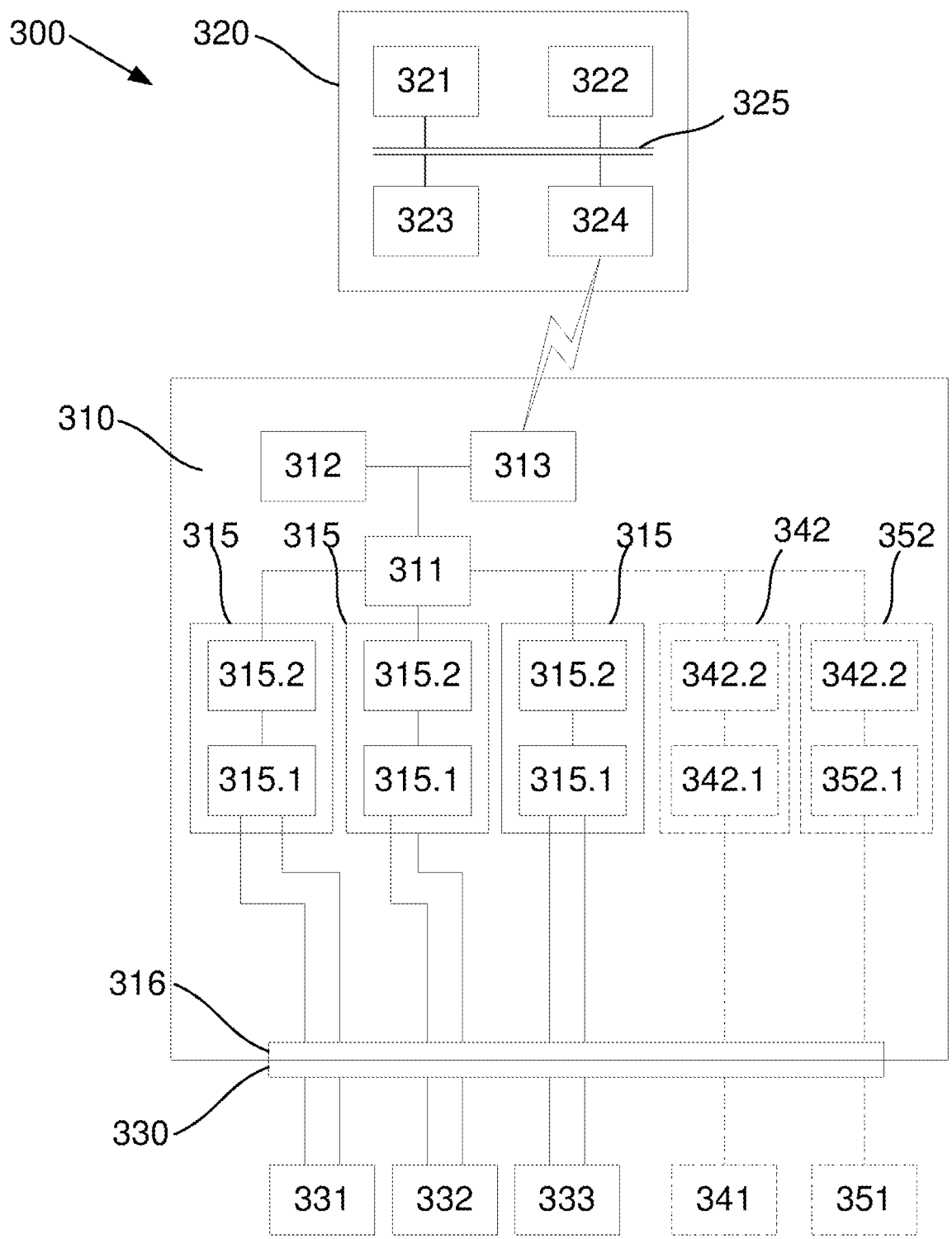
FIG. 3B is a schematic diagram of a second example of a system for use in monitoring muscle activity of a biological subject.

An alternative configuration is shown in FIG. 3B, in which multiple voltage sensors 315 are provided, with each being coupled to a respective pair of electrodes. In practice this configuration could be provided using a sequence of daisy chained ADCs 315.2, although any suitable configuration could be used. It will be appreciated that this configuration allows muscle activation signals to be measured from multiple pairs of electrodes in parallel, allowing measurements for multiple muscles and parts of muscles to be performed substantially simultaneously. This reduces overall measurement time, allowing repeated measurements to be performed at a higher rate, whilst also assisting with analysis of the signals, by allowing signals captured at an identical time to be analysed.

In each case, the measuring device 310 may also include a cardiac signal sensor 342 coupled to ECG electrodes 341, via the connector 330 and port 316. The cardiac signal sensor 342 typically includes an amplifier 342.1 and an analogue-to-digital convertor (ADC) 342.2, as well as an optional filter (not shown). Similarly the measuring device can include a respiratory signal sensor 352 coupled to a respiratory sensor 351 via the port 316 and connector 330. The nature of the respiratory sensor will vary depending on the preferred implementation and could include a sensor for measuring tension in an elastic belt extending round the chest or abdomen of the subject, or an inductance sensor that includes a conductive loop of wire attached to the subject. Example commercial inductance sensors include Philips Respironics zRIP inductive respiratory effort sensors. In either case, the respiratory signal sensor 352 typically includes an amplifier 352.1 and an analogue-to-digital convertor (ADC) 352.2, as well as an optional filter (not shown).

It will be appreciated that the cardiac and respiratory signal sensors 342, 352 are not essential, and in particular would only be required when used in conjunction with a garment, such as the shirt garment 110 including respective ECG electrodes 341 or respiratory sensor 351. Typically however standard measuring devices would be used in conjunction with the pants and shirt garments 120, 110, with the cardiac and respiratory signal sensors 342, 352 being unused if not required, thereby allowing common componentry to be used for the pant and shirt based measuring devices.

In use, the microprocessor 311 executes instructions in the form of applications software stored in the memory 312 to allow communication with the host device 320, as well as to control operation of the switching device 314, and at least partially process signals from the voltage sensor 315, the cardiac signal sensor 342 or respiratory signal sensor 352, providing an output based on the processed signals to the host device.

It will be appreciated from the above, that the measuring device 310 can include any suitable electronic processing device such as a microprocessor, microchip processor, logic gate configuration, firmware optionally associated with implementing logic such as an FPGA (Field Programmable Gate Array), or any other electronic device, system or arrangement.

The measuring device 310 can also include other ancillary sensor systems, such as a GPS (Global Position System), accelerometers, gyroscopes or the like, allowing additional parameters, such as movement of the subject to be sensed and used in determining indicators and/or monitoring activity.

The host device 320 typically includes a microprocessor 321, a memory 322, an input/output device 323, such as a keyboard and/or display, and an external interface 324, interconnected via a bus 325 as shown. In this example the external interface 324 can be utilised for connecting the host device 320 to peripheral devices, such as the measuring device 310, as well as other devices, such as communications networks, databases, other storage devices, or the like. Although a single external interface 325 is shown, this is for the purpose of example only, and in practice multiple interfaces using various methods (eg. Ethernet, serial, USB, wireless or the like) may be provided.

In use, the microprocessor 321 executes instructions in the form of applications software stored in the memory 322 to allow communication with the measuring device 310, for example to control operation of the measuring device 320, to receive outputs therefrom, and to at least partially process outputs to create and display representations of one or more indicators.

Accordingly, it will be appreciated that the host devices 320 may be formed from any suitable processing system, such as a suitably programmed PC, Internet terminal, laptop, or hand-held PC, and in one preferred example is either a tablet, or smart phone, or the like. However, it will also be understood that the host device 320 can be any electronic processing device such as a microprocessor, microchip processor, logic gate configuration, firmware optionally associated with implementing logic such as an FPGA (Field Programmable Gate Array), or any other electronic device, system or arrangement.

Examples of the processes for monitoring muscle activity will now be described in further detail. For the purpose of these examples it is assumed that the host device 320 is a smart phone, tablet, smartwatch or other similar computing device that executes a software application that allows for communication with one or more measuring devices 310, each of which is associated with a respective garment.

However, it will be appreciated that the above described configuration assumed for the purpose of the following examples is not essential, and numerous other configurations may be used. It will also be appreciated that the partitioning of functionality between the host devices 320, and the measuring devices 310 may vary. For example, the operation of the measuring device 310 could be controlled by a user via a user interface displayed on the measuring device, allowing the measurement process to be performed, with data indicative of measured signals being pushed to the host device, thereby allowing measurements to be performed without requiring the host device. It will also be appreciated that the host device could be connected to one or more other processing systems, such as part of a cloud or other distributed architecture.

Figure 4:
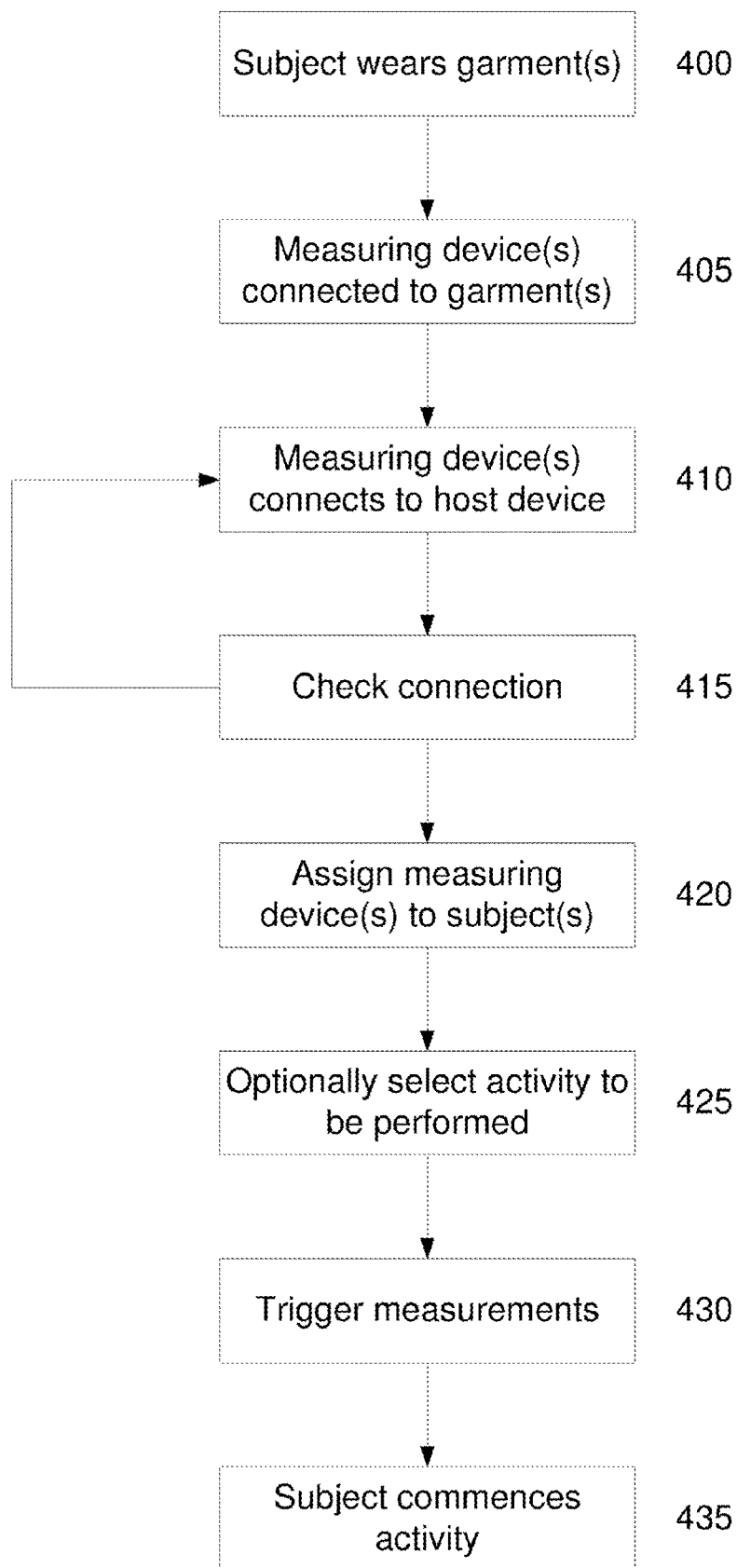
FIG. 4 is a flow chart of an example of a method for preparing the system to monitor muscle activity of a biological subject.

An example of a process for configuring the system for performing muscle measurement will now be described with reference to FIG. 4.

Initially, at step 400 the subject wears one or more garment(s), with respective measuring device(s) being connected to each garment at step 405. Thus, the connector 330 of each garment would be plugged into the port 316 of the respective measuring device 310, with this then being secured in the pocket of the garment.

At step 410, the measuring device(s) are connected to the host device 320. Thus can be achieved using any suitable technique, such as using a wireless communications protocol, such as Bluetooth™, or the like. Accordingly, the measuring device 310 can be turned on, and a software application on the host device launched, with the host device 320 being controlled by the application to cause the host device 320 to detect and connect to any active measuring devices 310 within range. It will be appreciated that as part of this a pairing procedure may be required to ensure the host device 320 is connecting to the correct measuring device(s) 310. As such pairing procedures are known in the art, this will not be described in any detail.

At step 415, the host device checks the connection with each measuring device 310, reconnecting at step 410 in the event that the connection is not operating successfully. This can be repeated until a successful connection is established, allowing the remaining procedures to be performed.

At step 420, the host device 320 can be used to assign a respective measuring device 310 to a particular subject. This is typically achieved by creating an association between a unique identifier of each measuring device 310, and an identifier associated with each subject, such as a name, or other suitable identifier. This allows a single host device to be used with measuring devices 310 associated with multiple subjects, so that a number of different subjects can be monitored using a single host device. This is particularly useful for scenarios such as team sports, where a coach or trainer could use a single host device to monitor the muscle activity of each team member. Alternatively, a medical practitioner could monitor many patients at once such as in a rehab or hospital environment.

Accordingly, the host device 320 can be used to present the user with a list of connected measuring devices 310, allowing the user to allocate these to respective individuals. Information regarding the association is then typically stored in a store, such as the memory 322, a remote database, or the like.

This process can also be used to ensure subject specific data is used during the analysis process. For example, a profile of each subject can be established, specifying subject characteristics, such as age, sex, weight, height, details of injuries, medical conditions and/or interventions, or the like. This information can be used when analysing recorded measurements, as will be described in more detail below.

At step 425, the user can optionally select an activity to be performed, allowing this information to be used in controlling the monitoring and/or analysis of muscle activity. The activities are generally predefined, for example by a supplier of the system and/or a user or medical practitioner or the like, and may be stored in a reference database, or the like, allowing the host device 320 to display a list of predefined activities. Alternatively, the user can custom define activities, for example specifying the type of activity and any requirements associated with the monitoring and/or analysis process to be used.

In the case of the monitoring process, the defined activity can be used to control the relative degree of monitoring of different muscle groups. For example, when performing squats, the primary muscles used are leg muscles. Thus, monitoring can be controlled to increase the sample rate for the leg muscles, whilst decreasing the sampling rate for lesser used muscles, such as arm muscles. This can be used to maximise the resolution of data collection for the primary muscles used in the specified activity.

In terms of analysing results, knowledge of the activity performed can be used to select a specific reference muscle activity pattern, which can be used when determining the indicators. For example, this allows the muscle activity of the subject collected whilst performing squats to be compared to an idealised muscle activity pattern for an individual with similar physical characteristics. This also allows signals to be analysed using appropriate techniques, such as magnitude and/or frequency analysis, depending on the indicator to be determined.

At step 430, the measurement process is triggered, for example by having the user select a "record now" option presented on the host device. At this point, the host device 320 communicates with the measuring device 310, causing the measuring device 310 to commence measurement of muscle activity. As part of this process, the host device 320 can transfer instructions to the measuring device 310, to control the measurement process, for example, instructing the measuring device to perform a particular measurement protocol. Once measurement has commenced, an indication of this can be provided, for example via the host device 320, or through a visual or audible indication on the measuring device 310, allowing the subject to be notified that activity can be commenced at step 435.

It will be appreciated however that connecting the measuring device to the host device as set out in steps 410 to 425 could be performed after an activity has been recorded. In this instance, the user could simply activate the measuring device, for example using a suitable input button provided on the device, causing measurements to be performed. In this case, connection to the host device may only occur after the measurements have been recorded, or could be performed automatically during the activity, and reference to connection of the measuring and host devices prior to commencing activity is not intended to be limiting.

Figure 5A:
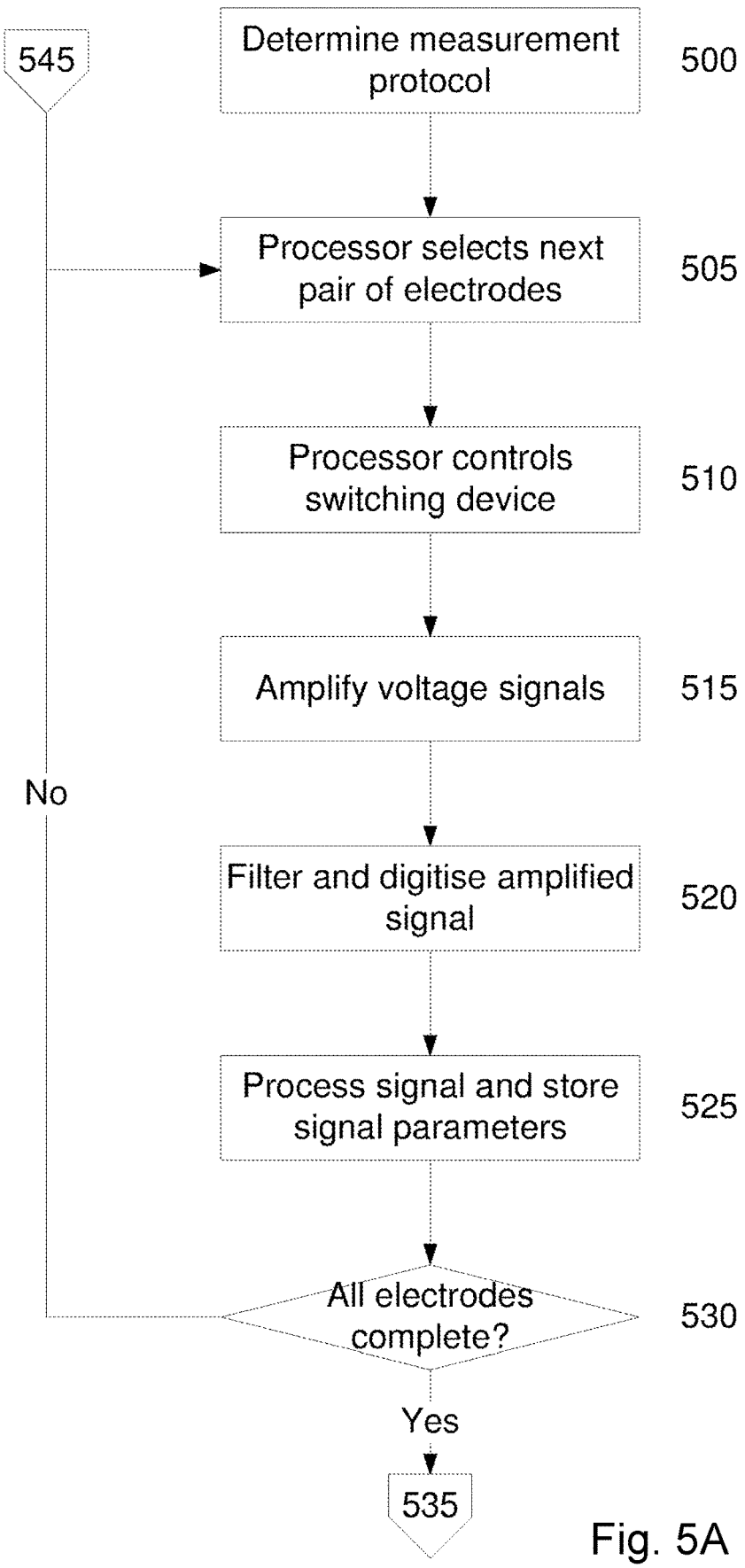
FIGS. 5A and 5B are a flow chart of a specific example of a method for monitoring muscle activity of a biological subject using the system of FIG. 3.
Figure 5B:
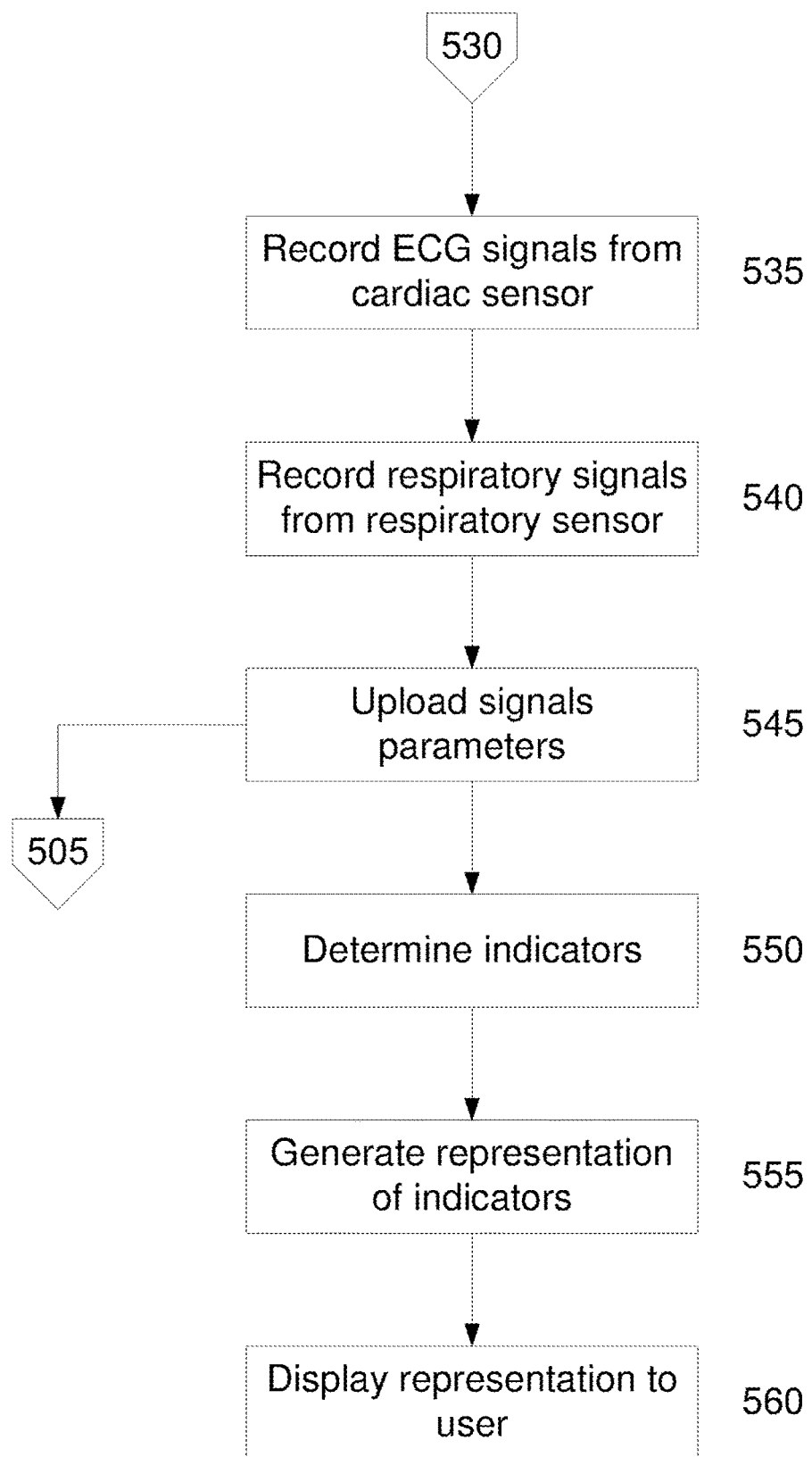

The process of monitoring muscle activity after commencing activity will now be described with reference to FIGS. 5A and 5B.

In this example, at step 500, the measuring device 310 determines the measurement protocol to be used for the sequence of measurements. The measurement protocol is typically retrieved from memory 312 based on instructions provided by the host device 320, as described above with respect to FIG. 4, although alternatively may be received directly from the host device 320, depending on the preferred implementation. Alternatively, the measurement protocol could be a standard protocol implemented when the measuring device is activated, or could be selected from protocols stored locally in the memory 312 based on manual input commands, for example in the event the measurement process is triggered without using the host device 320.

At step 505, the processor 311 selects a next pair of electrodes from which a measurement is to be taken, and controls the switching device 314 accordingly at step 510, to thereby couple the respective pair of electrodes to the voltage sensor 315. It will be appreciated that these steps are not required in the event that the apparatus of FIG. 3B is used, in which case measurements are performed for each pair of electrodes simultaneously.

The potential difference between the electrodes is amplified by the amplifier 315.1 at step 515, before being filtered and digitised at step 520. It will be appreciated that the measurement is typically performed over a predetermined time period, such as a few milliseconds, allowing the frequency and magnitude of the potential difference to be captured. The exact time period used will depend on the preferred implementation, and/or measurement protocol, as will be appreciated by persons skilled in the art.

The digitised voltage signals are provided to the processor 311, which typically at least partially analyses the signals to determine signal parameters, which are then stored in the memory 312 at step 525. It will be appreciated that the signals themselves can also be stored, although this is not necessary and hence will typically depend on storage availability.

The nature of the processing performed by the processor 311 will vary depending on the preferred implementation, and can include for example performing a Fourier analysis to determine the magnitude of the voltage between electrodes for different frequency components within the measured signal. In this regard, the measurement protocol can define the processing to be performed and in particular any signal parameters that are to be determined, such as frequency components of interest and examples of types of analysis that can be performed are described in "*Techniques of MG signal analysis: detection, processing, classification and applications*" by M. B. I. Raez, M. S. Hussain, 1 and F. Mohd-Yasin in Biol Proced Online. 2006; 8: 11-35.

In any event, at step 530 the processor 311 determines if all required measurements have been completed, and if not returns to step 510 to control the switching device and record measurements for the next pair of electrodes. Again it will be appreciated that this is not required in the event that measurements are performed on all pairs of electrodes simultaneously.

At steps 535 and 540 the processor 311 will optionally record ECG and respiratory signals from the cardiac and respiratory sensors in a similar manner. It will be appreciated that in practice this is typically performed in parallel with the process described in steps 510 to 530, so that cardiac and respiratory signals are recorded concurrently with collection of muscle activity signals.

Once muscle activity and optionally ECG and respiratory signals have been recorded, these can be used to determine indicators. This process can be performed in a variety of manners, and could include calculating the indicators in the processor 311. More typically however, the signal parameters determined at step 525 are uploaded to the host device for analysis at step 545. This allows processing to be distributed between the measuring device 310 and host device 320 and also avoids the need for references and calculation techniques to be stored on the measuring device. However, this is not essential and any suitable distribution of processing can be used.

Whilst upload of information can be performed once the measurement process has been concluded, more typically this is performed whilst collection of data continues, with the processor 311 returning to step 505 to select a next electrode pair, allowing indicators to be calculated and displayed dynamically as activities are ongoing. This is particularly useful in monitoring the ongoing effect of the activities being performed on muscle activity. In particular, this allows real-time feedback to be provided to the subject as the activities are performed.

At step 550, the host device 320 determines various indicators, depending for example on the measurement protocol being performed, and examples of the derivation of specific indicators will be described in more detail below.

Once indicators have been determined, at step 555, the host device 320 generates a representation of the indicators, allowing this to be displayed to a user. The nature of the representation will vary depending on the preferred implementation, user settings and the nature of the indicator.

In one example, the representation can include a simple alphanumeric indicator, indicative of a measured activity for one or more muscles and/or muscle groups. However, more typically the representation includes a graphical representation of a human body, illustrating one or more muscle groups, and showing visual indications of the indicators thereon. This could include colour coding of parts of individual muscles, or muscle groups to illustrate a level of activity relative to a baseline or other reference, showing a graph indicative of the level of ability, or the like. It will be appreciated that by having indicators indicative of muscle activity measured and displayed in real time can help provide useful feedback to the subject performing the activity, in particular allowing the individual to assess whether the activity is being performed effectively, and potentially to identify the onset of fatigue and/or the potential for injury.

Figure 6:
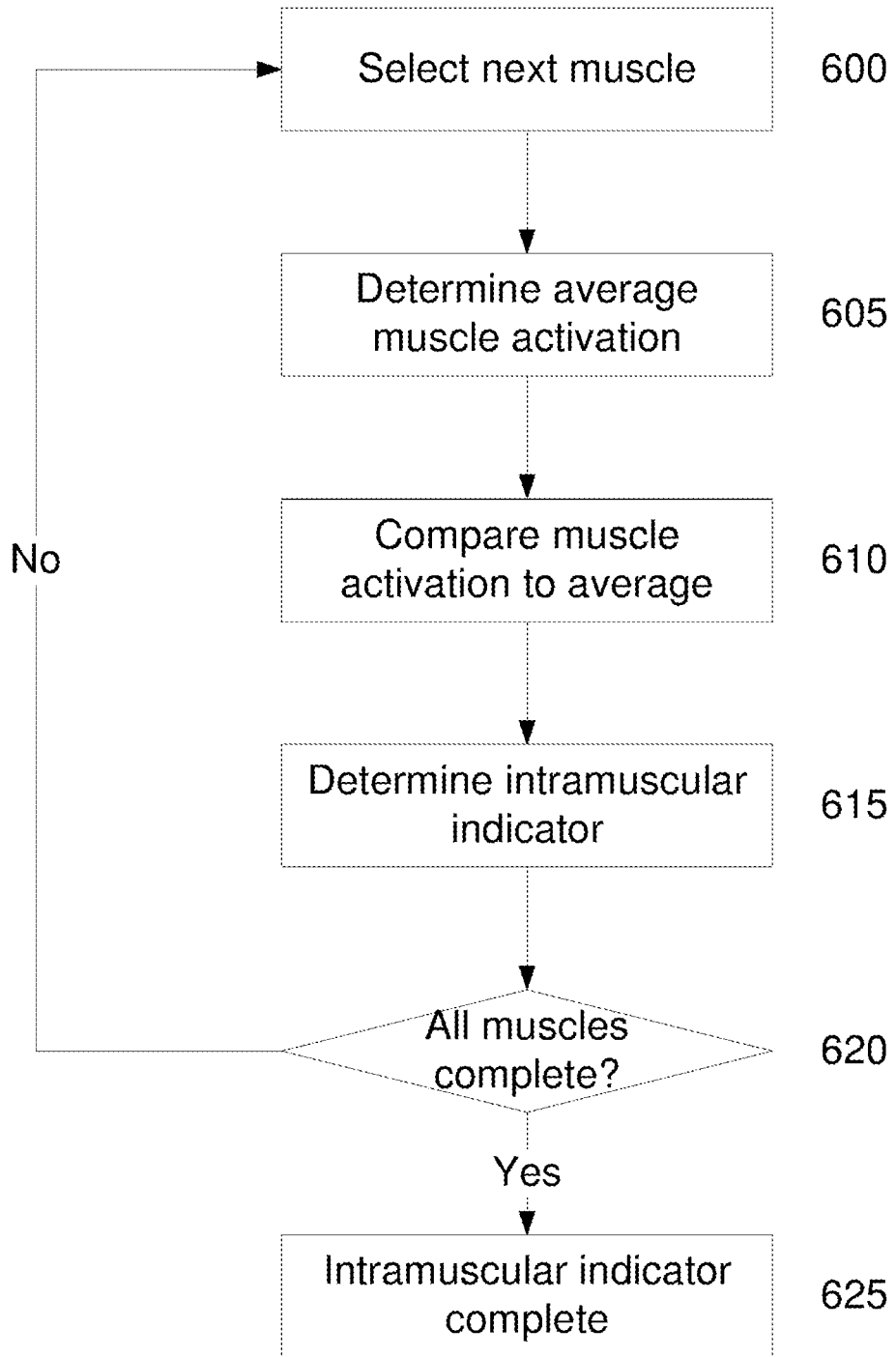
FIG. 6 is a flow chart of an example of a method for determining an intramuscular indicator.

An example of the process for determining an intramuscular indicator will now be described with reference to FIG. 6.

In this example, at step 600 a next muscle or muscle group is selected, with an average activation for the respective muscle or muscle group being determined at step 605. In this example, the activation is typically based on the magnitude of the potential difference between pairs of electrodes, averaged for each pair of electrodes for the given muscle or muscle group. It will be appreciated that averaging could be performed in any appropriate manner, and in one example this could be achieved based on an average derived from measurements made between end points, and between end and mid points of the muscle. This reduces the number of measurements required to determine an average, whilst still allowing a reasonable accurate average to be determined.

At step 610, the muscle activation for each part of the muscle or muscle group, as determined based on the magnitude of the potential difference between a pair of electrodes, is compared to the average activation. The results of the comparison are used to determine the intramuscular indicator at step 615, specifically by identifying parts of the muscle or muscle group that are demonstrating an activation beyond one or more standard deviations of the average cell-cell muscle activation. At step 620, it is determined if all muscles are complete, and if not the process returns to step 600, otherwise the process ends at step 625.

The intramuscular indicator can be of any form and is generally used to identify parts of the muscle or muscle group which are demonstrating above or below average activation, which is in turn used to identify potential muscle damage. For example, in the event that part of the muscle is damaged, this could be under activating, whilst over activating parts of a muscle could indicate the potential for injury.

In one example, the indicator is used to generate a representation in the form of a map of the respective muscle, with the location of over or under active parts of the muscle being identified thereon. For example, this could include colour coding to indicate the degree of under or over activation, as compared to the average activation.

Figure 7:
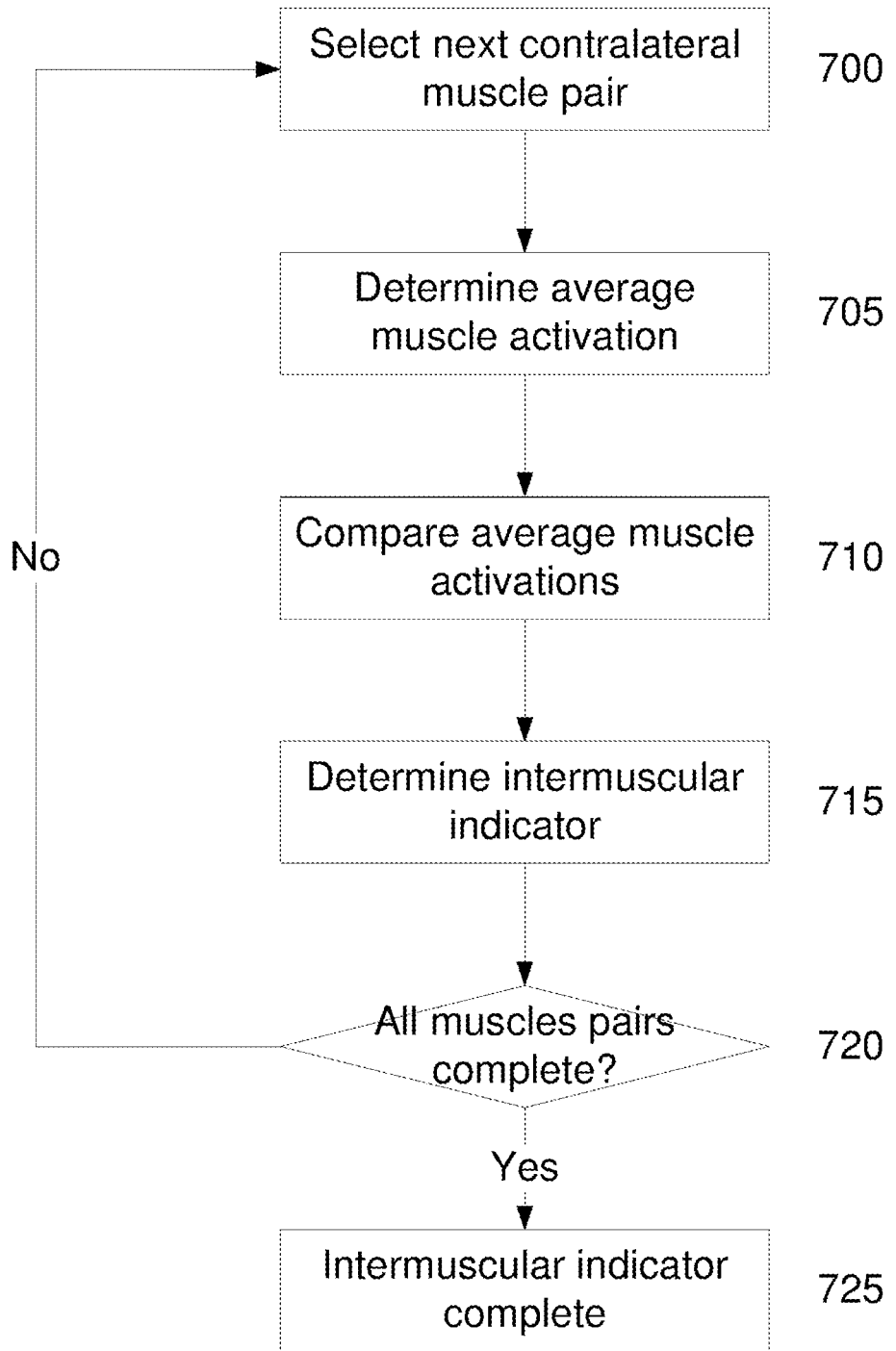
FIG. 7 is a flow chart of an example of a method for determining an intermuscular indicator.

An example of the process for determining an intermuscular indicator will now be described with reference to FIG. 7.

In this example, at step 700 a next contralateral muscle pair is selected. In this regard, the contralateral muscle pair is a pair of muscles or muscle groups positioned on contralateral parts and typically limbs, of the subject's body.

At step 705 an average activation for each muscle in the pair is determined, with this again being performed by averaging the magnitude of the potential difference for each pair of electrodes for the respective muscle or muscle group.

At step 710, the average activation for each muscle is compared, with a difference being used to determine the intermuscular indicator at step 715. At step 720, it is determined if each pair is complete, and if not the process returns to step 700. Otherwise, the process ends at step 720.

In this instance, the intermuscular indication is indicative of any disparate average activation between contralateral muscles, and is used to identify any imbalance in muscle activation in the subject. It will be appreciated that this indicator is generally only determined when the user is performing an activity that places symmetrical loads on the muscles.

Figure 8:
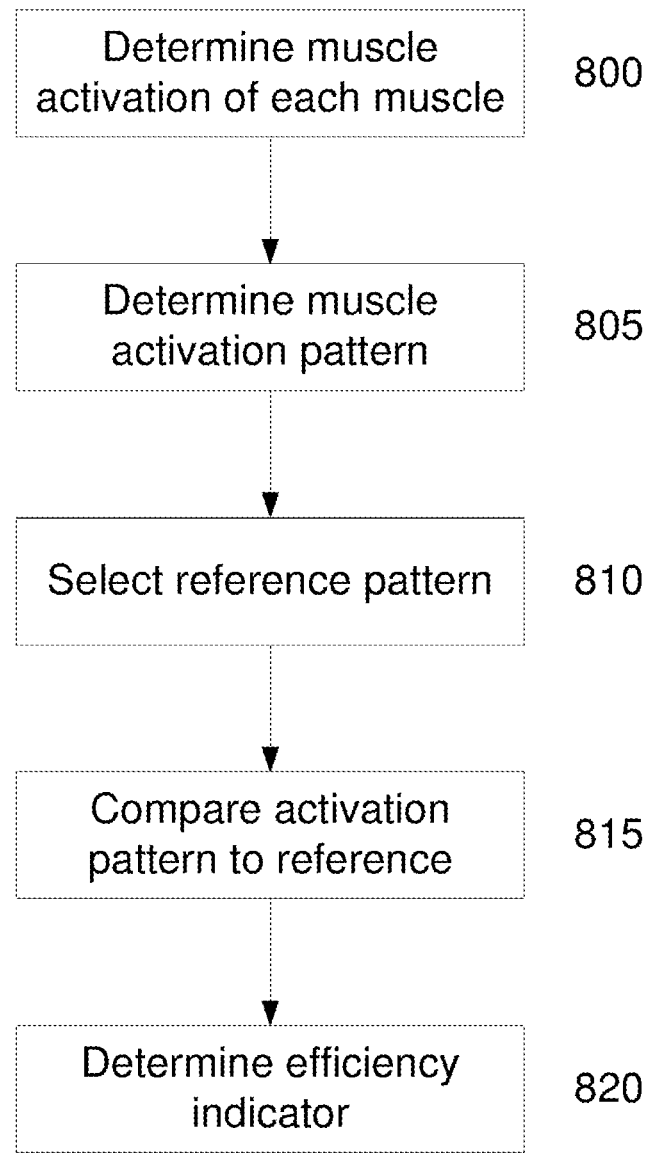
FIG. 8 is a flow chart of an example of a method for determining an efficiency indicator; and, FIG. 9 is a flow chart of an example of a method for determining a fatigue indicator.

An example of the process for determining an efficiency indicator will now be described with reference to FIG. 8.

In this example, at step 800 a muscle activation for each muscle or muscle group is determined. Again this is typically performed by averaging the magnitude of the potential difference for each pair of electrodes for the respective muscle or muscle group.

At step 805, a muscle activation pattern is determined, with this typically representing a proportion of the overall muscle activity attributable to each muscle.

At step 810, a reference activation pattern is selected. The reference activation pattern can be determined based on a study of individuals in a sample population when the individuals are performing the same activity as the subject. The individuals are typically selected to have similar physical characteristics, such as sex, ethnicity, age, weight, height, body mass index, or the like, and are typically assessed as healthy individuals. Thus, it will be appreciated that the reference activation pattern represents an idealised activation pattern for the subject when performing the given activity.

However, additionally and/or alternatively, the reference muscle activation pattern could be defined by a user. For example, if the user is a practitioner, such as a physiotherapist, doctor, trainer, or the like, they may wish to define a reference activation pattern for a subject to achieve an end goal. This could be part of a treatment program, for example to assist in recovery from injury, or with a view to improving strength or movement. In this instance, it will be appreciated that the practitioner might be better able to determine a desired activation pattern based on an understanding of the requirements for the subject, which is therefore more appropriate than a fixed defined pattern. However, to assist in avoiding injury, the reference patterns could be tailored within defined limits, allowing some variation between subject goals or requirements to be accommodated, whilst ensuring the patterns that could be adverse to the subject are avoided.

As part of this, the system can allow different reference activation patterns to be shared, so for example, if a practitioner develops a pattern that is particularly effective at treating a particular injury or condition, or achieving a particular training goal, this can be shared with other users.

However, it will be appreciated that the use of "standard" defined reference patterns can also assist in ensuring consistency in assessment or treatment of subjects. This can ensure that biases inherent when different individuals monitor or treat a subject, are overcome or obviated, maximising the chance of issues being appropriately identified and addressed.

An example muscle activation pattern when performing squats is shown in Table 1 below, with the numbers representing a relative level of activity, defined to sum to 1.

TABLE 1

| Muscle | Left | Right |
| --- | --- | --- |
| Gluteals | 0.4 | 0.4 |
| Quadriceps | 0.175 | 0.175 |
| Hamstrings | 0.225 | 0.225 |
| Adductors | 0.1 | 0.1 |
| Calf | 0.1 | 0.1 |

At step 815, the measured activation pattern is compared to the reference activation pattern, with this being used to determine an efficiency indicator at step 820. The efficiency indicator could be used to identify muscles or muscle groups that are over or under activating compared to the reference activation pattern, which in turn can identify issues either with the subject muscles, and/or the technique the subject is using when performing the respective activity. Thus, this can be used to identify if the subject is performing the activity in the most efficient manner.

Figure 9:
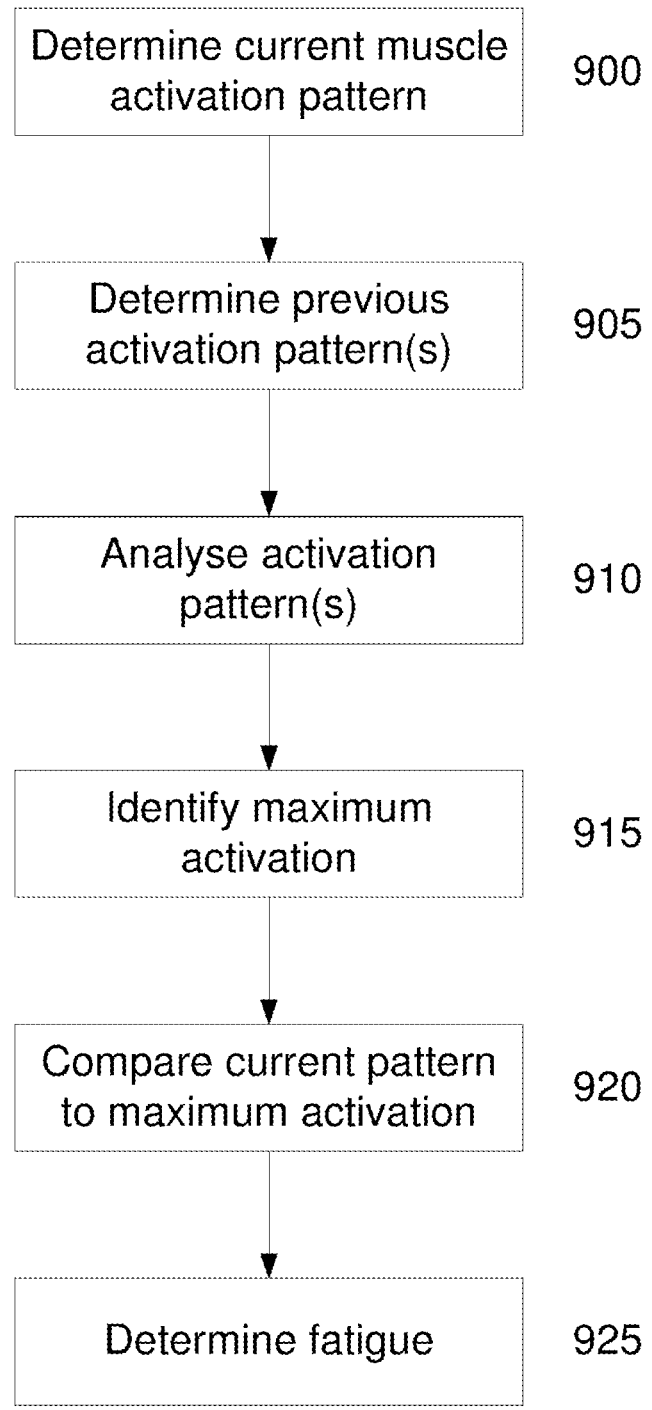

An example of the process for determining a fatigue indicator will now be described with reference to FIG. 9.

In this example, at step 900 a current muscle activation pattern is determined for the subject. In this example, the activation pattern is typically based on the frequency of muscle firing and/or the wave complex analogous to the QRS complex of an ECG signal.

At step 905, previous historical activation patterns recorded for the subject, when performing the same activity, are determined, for example by retrieving these from a store, such as a memory, a database, or the like.

At step 910, the previous activation patterns are analysed to identify a maximum and/or average historical activation pattern at step 915. The current activation pattern being compared to the historical maximum and/or average activation pattern at step 920, with deviations from the average and/or maximum being used to determine a fatigue indicator at step 925. Thus, this allows the changes in activation, and in particular changes in the frequency of activation over time to be monitored as a subject repeatedly performs a given activity, thereby allowing muscle fatigue to be assessed.

The fatigue indicator could also take into account additional factors, such absolute or relative changes in heart and/or respiratory rate, distance travelled or other movements, as determined from appropriate ones of the sensors.

It will also be appreciated that indicators indicative of a total activity for a defined period, such as a day, week, or specific workout period, could be determined, and used as part of a fitness monitoring program. This could include using muscle activity together with overall indicators of movement, heart rate and respiration, to calculate calories burned during an exercise program, with this being used as part of a broader fitness monitoring program, as will be appreciated by persons skilled in the art.

Accordingly, the above described system allows measurements of muscle activity to be performed through the use of wearable garments incorporating arrays of electrodes, which allow EMG signals indicative of muscle activation to be monitored. This in turn allows muscle activity to be measured whilst performing activities, including but not limited to sporting activities, exercises, and/or day-to-day activities. Data collected can be analysed allowing a number of different indicators to be derived, which can in turn provide insights into the muscle function and execution of the activities by the subject. This can include, but is not limited to identifying damage to muscles, imbalance in use of muscles, optimising the efficiency of muscle usage during defined activities, and detection of fatigue. The indicators can be displayed in real time as activities are performed and/or can be recorded and subsequently reviewed to allow for longitudinal study of muscle activity.

It will therefore be appreciated that the above described system can be used in a wide range of circumstances, including but not limited to training of subjects for sporting activities, monitoring subject during activities to identify the potential for or onset of injuries, and studying subjects in a medical context to identify muscle related conditions, such as muscle wastage, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A system for monitoring a biological subject, the system including:

a) a garment including a number of arrays of electrodes positioned on the garment, wherein the arrays of electrodes are positioned on the garment so that when the garment is worn by the biological subject, the electrodes configured to contact of the biological subject and generate electrical signals indicative of electrical potentials within respective muscles of the biological subject, wherein each of the arrays of electrodes includes a plurality of electrodes arranged in a grid; and,
b) at least one electronic processing device configured to:
i) process signals from the electrodes in each of the arrays of electrodes to determine a muscle activation for one or more parts of the respective muscles;
ii) use the muscle activation to determine at least one muscle indicator indicative of a muscle activity of the biological subject, wherein the at least one muscle indicator is based on results of a comparison of a muscle activation pattern for the muscle activation to a reference muscle activation pattern which represents an idealised activation pattern for the biological subject when performing a given activity;
iii) generate a representation at least partially based on the at least one muscle indicator; and,
iv) cause the representation to be communicated to a user.

2. The system according to claim 1, wherein the electrodes are at least one of:
a) conductive fabric electrodes woven into the garment;
b) dry electrodes provided in the garment;
c) silver plated nylon electrodes; and,
d) silver plated nanowire electrodes.

3. The system according to claim 1, wherein each electrode at least one of:
a) has a surface area that is at least one of:
i) between 0.75 cm² and 1.5 cm';
ii) about 0.75+0.25 cm2:
ii) about 1.0+0.25 cm2;
iv) about 1.25+0.25 cm2;
v) about 1.5+0.25 cm2;
vi) about 1.75+0.25 cm2;
vii) about 2.0+0.25 cm2;
viii) about 2.5+0.5 cm2:
ix) about 1 cm2,
b) is spaced by at least one of:
i) between 0.5 cm and 2.0 cm;
ii) between 0.75 cm and 1.75 cm;
iii) between 1.0 cm and 1.5 cm;
iv) about 0.75+0.25 cm;
v) about 1.0+0.25 cm;
vi) about 1.25+0.25 cm; and,
vii) about 1.5+0.25 cm;
c) is electrically connected to a connector, the connector being for coupling the electrodes to the at least one processing device; and,
d) is electrically connected to the connector via nanowires woven into the garment.

4. The system according to claim 1, wherein the garment at least one of:
a) includes a pocket for receiving the at least one processing device, a connector being provided at least partially within the pocket;
b) includes pants for covering at least a groin and upper legs of the biological subject; and,
c) includes a shirt for covering at least a torso of the biological subject;
d) includes elasticated material to thereby urge the electrodes against the biological subject's skin; and,
e) is made of at least one of:
i) polyamides;
ii) polyester; and,
iii) elastane.

5. The system according to claim 1, wherein the representation includes at least one of:
i) an alphanumeric indication of the at least one muscle indicator;
ii) a graphical representation of the muscle activation pattern for at least one muscle; and,
ii) a graphical representation of the results of a comparison of the muscle activation pattern to the reference muscle activation pattern.

6. The system according to claim 1, wherein the at least one muscle indicator is an efficiency indicator, wherein the efficiency indicator is indicative of a relative efficiency of muscle activation of muscles when performing a task.

7. The system according to claim 1, wherein each of the arrays of electrodes is aligned with a particular muscle or muscle group and wherein the particular muscle or muscle group include at least one of:
a) trapezius;
b) rhomboids;
c) latissimus dorsi;
d) erector spinae;
e) rotator cuff muscles (including supraspinatus, infraspinatus, subscapularis, *teres* minor/major);
f) forearm extensors/flexors;
g) tibialis anterior/posterior;
h) thoracic paraspinals;
i) lumbar paraspinals;
j) biceps;
k) triceps;
l) Quadriceps;
m) hamstrings;
n) adductors;
o) gluteals;
p) calves;
q) abdominals;
r) deltoids; and,
s) pectorals.

8. The system according to claim 1, wherein the garment includes a plurality of the arrays of electrodes, and each of the plurality of the arrays of electrodes is aligned with a particular muscle or muscle group.

9. A system for monitoring muscle activity of a biological subject, the system including:
a) at least one garment including a number of arrays of electrodes positioned on the garment so that when the garment is worn by the biological subject, the electrodes are configured to contact of the biological subject and generate electrical signals indicative of electrical potentials within respective muscles of the biological subject, wherein each of the arrays of electrodes includes a plurality of electrodes arranged in a grid; and,
b) at least one processing device that:
i) determines a muscle activation pattern indicative of a muscle activation of each of a number of muscles;
ii) compares the muscle activation pattern to a reference muscle activation pattern; and,
ii) determines an efficiency indicator at least in part using results of the comparison, wherein the efficiency indicator is indicative of a relative efficiency of muscle activation of muscles when performing a task.

10. The system according to claim 9, wherein the at least one processing device:
a) determines an activity being performed by the biological subject at least one of:

i) by analysing the muscle activation patterns; and,
ii) in accordance with user input commands; and,
b) selects one of a number of predefined reference activation patterns at least partially in accordance with the determined activity; and,
c) compares the muscle activation pattern to the selected reference muscle activation pattern.

11. The system according to claim 9, wherein the at least one processing device:
a) determines a current muscle activation pattern indicative of the muscle activation of each of the number of muscles;
b) determines previous muscle activation patterns;
c) identifies an historical activation pattern based on at least one of a mean and maximum of the previous muscle activation patterns;
d) compares the current muscle activation pattern to the historical activation pattern; and,
e) determines a fatigue indicator at least in part using results of the comparison.

12. The system according to claim 9, wherein the system includes a measuring device, the measuring device including:
a) a voltage sensor coupled to the electrodes for sensing the electrical potentials between pairs of electrodes; and,
b) the at least one processing device coupled to the voltage sensor for receiving signals indicative of the sensed voltages.

13. The system according to claim 12, wherein the voltage sensor includes:
a) a differential amplifier for amplifying analogue electrical signals obtained from the pair of electrodes; and,
b) an A/D convertor for converting an amplified differential voltage into a digital voltage signal, the digital voltage signal being provided to the at least one processing device for processing.

14. The system according to claim 12, wherein the measuring device includes at least one of:
a) a filter for filtering the electrical signals;
b) an anti-aliasing front end analogue filter; and,
c) a digital bandpass filter.

15. The system according to claim 12, wherein the system includes:
a) a first electronic processing device configured to be attached to or worn by the biological subject that:
i) acquires the electrical signals from the voltage sensor;
ii) at least partially processes the electrical signals; and,
b) a second processing device that wirelessly communicates with the first processing device and displays a representation at least partially based on at least one muscle indicator.

16. The system according to claim 9, wherein the system includes an ECG sensor for sensing cardiac activity of the biological subject and wherein the at least one electronic processing device:
a) acquires signals from the ECG sensor; and,
b) determines a cardiac indicator indicative of cardiac activity of the biological subject.

17. The system according to claim 9, wherein the system includes a respiratory sensor for sensing respiratory activity of the biological subject and wherein the at least one electronic processing device:
a) acquires signals from the respiratory sensor; and,
b) determines a respiratory indicator indicative of respiratory activity of the biological subject.

18. The system according to claim 9, wherein the at least one electronic processing device determines an activity indicator indicative of an overall activity of the biological subject using:
a) at least one muscle indicator; and,
b) at least one of:
i) a cardiac indicator indicative of cardiac activity of the biological subject; and,
ii) a respiratory indicator indicative of respiratory activity of the biological subject.

19. A method for monitoring muscle activity of a biological subject, the method including, in at least one processing device:
a) determining a muscle activation pattern indicative of the muscle activation of each of a number of muscles;
b) comparing the muscle activation pattern to a reference muscle activation pattern; and,
c) determining an efficiency indicator at least in part using results of the comparison, wherein the efficiency indicator is indicative of a relative efficiency of muscle activation of muscles when performing a task.

* * * * *

UNITED STATES PATENT AND TRADEMARK OFFICE
CERTIFICATE OF CORRECTION

PATENT NO. : 11,832,950 B2  
APPLICATION NO. : 17/174302  
DATED : December 5, 2023  
INVENTOR(S) : Nicholas Dodemont Page 1 of 1

It is certified that error appears in the above-identified patent and that said Letters Patent is hereby corrected as shown below:

In the Claims

In Claim 3, Column 21, Line 31, "cm1" should read -- cm2 --.

In Claim 3, Column 21, Line 33, "ii) about" should read -- iii) about --.

In Claim 3, Column 21, Lines 32 through 38 and Lines 44 through 47, each occurrence of "+" between the two values should read -- ± --.

In Claim 5, Column 22, Line 7, "ii) a graphical" should read -- iii) a graphical --.

In Claim 7, Column 22, Line 31, "Quadriceps" should read -- quadriceps --.

In Claim 9, Column 22, Line 48, "to contact of the biological subject" should read -- to contact the biological subject --.

In Claim 9, Column 22, Line 59, "ii) determines an" should read -- iii) determines an --.

Signed and Sealed this  
Twenty-seventh Day of August, 2024

Katherine Kelly Vidal  
*Director of the United States Patent and Trademark Office*